US 11,129,752 B2

(12) United States Patent
Huang et al.

(10) Patent No.: US 11,129,752 B2
(45) Date of Patent: Sep. 28, 2021

(54) BREATHABLE STRUCTURAL WEB AND BREATHABLE STRUCTURAL WEB-FORMING APPARATUS

(71) Applicants: Chen-Cheng Huang, Taipei (TW); Pao-Hao Huang, Taipei (TW); Pao-Han Huang, Taipei (TW)

(72) Inventors: Chen-Cheng Huang, Taipei (TW); Pao-Hao Huang, Taipei (TW); Pao-Han Huang, Taipei (TW)

( * ) Notice: Subject to any disclaimer, the term of this patent is extended or adjusted under 35 U.S.C. 154(b) by 577 days.

(21) Appl. No.: 15/835,424

(22) Filed: Dec. 7, 2017

(65) Prior Publication Data

US 2018/0098886 A1 Apr. 12, 2018

Related U.S. Application Data

(62) Division of application No. 14/687,522, filed on Apr. 15, 2015, now Pat. No. 9,877,876.

(30) Foreign Application Priority Data

Apr. 18, 2014 (TW) .................................. 103114210

(51) Int. Cl.
*A61F 13/15* (2006.01)
*D04H 1/732* (2012.01)
(Continued)

(52) U.S. Cl.
CPC .. *A61F 13/15203* (2013.01); *A61F 13/15707* (2013.01); *A61F 13/49* (2013.01); *A61F 13/5121* (2013.01); *A61F 13/51104* (2013.01); *B29C 41/28* (2013.01); *B29C 41/32* (2013.01); *B29C 41/50* (2013.01); *B29C 48/08* (2019.02); *B29C 48/11* (2019.02); *B29C 48/12* (2019.02);

*D04H 1/724* (2013.01); *D04H 1/732* (2013.01); *D04H 3/16* (2013.01); *D04H 13/00* (2013.01); *A61F 2013/15552* (2013.01);
(Continued)

(58) Field of Classification Search
CPC ......... B29C 48/08; B29C 48/11; B29C 48/12; B29C 41/28; B29C 41/32; B29C 41/50; D04H 1/724; D04H 1/732; D04H 13/00; D04G 3/16
USPC .......................................................... 428/167
See application file for complete search history.

(56) References Cited

U.S. PATENT DOCUMENTS 3,034,180 A 5/1962 Greiner et al.
4,741,941 A 5/1988 Englebert et al.
(Continued)

FOREIGN PATENT DOCUMENTS

EP 2095802 A1 * 9/2009 ......... A61F 13/5126

*Primary Examiner* — Vincent Tatesure
(74) *Attorney, Agent, or Firm* — Hamre, Schumann, Mueller & Larson, P.C.

(57) ABSTRACT

A breathable structural web includes a layered structure having at least a layer of a non-woven material. The layered structure includes a base layer portion that has opposite first and second sides, a plurality of hollow protrusions that are disposed at the first side and that protrude and that are tapered from the base layer portion in a first direction, and a plurality of indented portions that are disposed at the second side, that extend from the base layer portion in a second direction opposite to the first direction, and that respectively define a plurality of recesses which open in the first direction. The hollow protrusions are scattered among the indented portions.

11 Claims, 15 Drawing Sheets

(51) Int. Cl.
    *D04H 1/724*     (2012.01)
    *D04H 3/16*     (2006.01)
    *B29C 48/08*     (2019.01)
    *B29C 48/11*     (2019.01)
    *B29C 48/12*     (2019.01)
    *A61F 13/511*     (2006.01)
    *A61F 13/512*     (2006.01)
    *A61F 13/49*     (2006.01)
    *B29C 41/28*     (2006.01)
    *B29C 41/32*     (2006.01)
    *B29C 41/50*     (2006.01)
    *D04H 13/00*     (2006.01)
    *B29K 101/12*     (2006.01)
    *B29L 31/48*     (2006.01)

(52) U.S. Cl.
    CPC . *A61F 2013/15715* (2013.01); *B29K 2101/12* (2013.01); *B29L 2031/4878* (2013.01)

(56) References Cited

U.S. PATENT DOCUMENTS

| | | |
|---|---|---|
| 5,575,874 A | 11/1996 | Greisbach, III et al. |
| 9,011,135 B2 | 4/2015 | Huang et al. |
| 2011/0212321 A1 | 9/2011 | Cakmak et al. |
| 2012/0066855 A1 | 3/2012 | Schmidt et al. |
| 2013/0285294 A1 | 10/2013 | Huang et al. |

\* cited by examiner

BREATHABLE STRUCTURAL WEB AND BREATHABLE STRUCTURAL WEB-FORMING APPARATUS

CROSS-REFERENCE TO RELATED APPLICATION

This application is a divisional application of U.S. patent application Ser. No. 14/687,522 (filed on Apr. 15, 2015), which claims priority of Taiwanese Patent Application No. 103114210 (filed on Apr. 18, 2014). This application claims the benefits and priority of all these prior applications and incorporates by reference the contents of these prior applications in their entirety.

FIELD

The disclosure relates to a breathable structural web-forming apparatus and a breathable structural web having at least a layer of a non-woven membrane and a layered structure including a base layer portion and a plurality of hollow protrusions protruding from the base layer portion.

BACKGROUND

Non-woven membranes are made from polymers through techniques, such as melt blown or melt spun techniques. In melt blown techniques, molten fibers are formed and are discharged from a spinneret, and are stacked and bonded together to form the non-woven membrane. The non-woven membrane thus formed has a plurality of pores, which renders the non-woven membrane to be permeable to air and water and useful in applications, such as diapers, napkins, cloths, filters, etc. However, the pores in the non-woven membrane are randomly formed, have various sizes, and do not have a defined directivity for flow of water or liquid, which limits the application of the non-woven membrane.

SUMMARY

Therefore, an object of the disclosure is to provide a breathable structural web that can overcome the aforesaid drawback associated with the prior art.

According to one aspect of the disclosure, there is provided a breathable structural web that comprises a layered structure including at least a layer of a non-woven material. The layered structure includes a base layer portion that has opposite first and second sides, a plurality of hollow protrusions that are disposed at the first side and that protrude and that are tapered from the base layer portion in a first direction, and a plurality of indented portions that are disposed at the second side, that extend from the base layer portion in a second direction opposite to the first direction, and that respectively define a plurality of recesses which open in the first direction. The hollow protrusions are scattered among the indented portions.

According to another aspect of the disclosure, there is provided a breathable diaper that comprises the aforesaid breathable structural web and an absorbent stacked on the breathable structural web.

According to yet another aspect of the disclosure, there is provided a breathable structural web-forming apparatus that comprises: a rotary member defining a rotation axis and rotatable about the rotation axis; a screen mold supported on the rotary member and co-rotatable with the rotary member, the screen mold including a screen body and a plurality of tapered projections, the screen body having first and second sides and a plurality of screen holes, the tapered projections protruding and being tapered from the first side of the screen body; a spinneret that is disposed adjacent to the first side of the screen body and opposite to the second side of the screen body, and that is configured to discharge molten fibers toward the first side of the screen body; and a suction box that is disposed adjacent to the second side of the screen body and opposite to the first side of the screen body, and that is configured to draw the molten fibers to fit into the screen holes.

BRIEF DESCRIPTION OF THE DRAWINGS

In drawings which illustrate embodiments of the invention.

DETAILED DESCRIPTION

Figure 1:
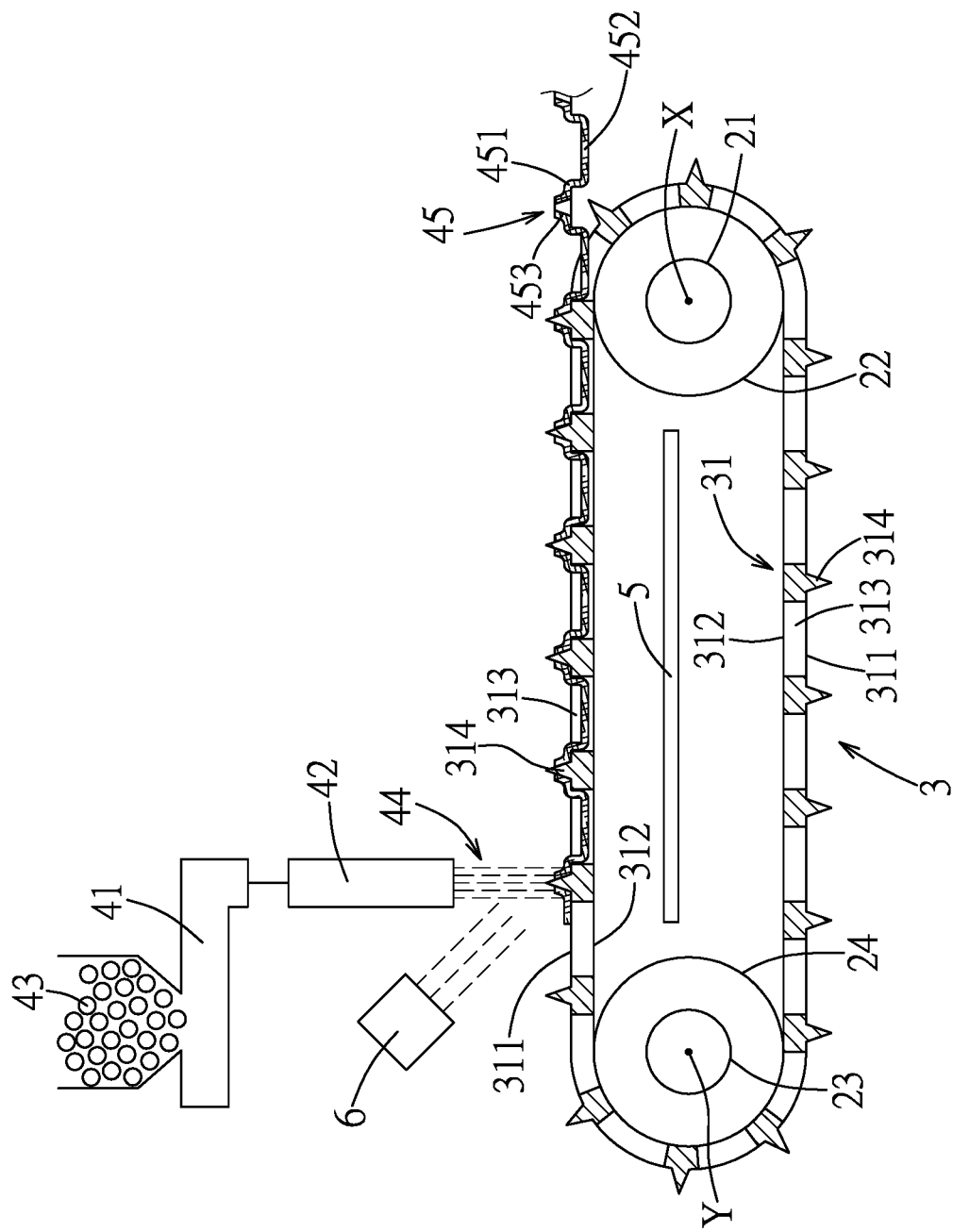
FIG. 1 is a schematic view of a breathable structural web-forming apparatus used for making the first embodiment of a breathable structural web according to the disclosure.

Before the disclosure is described in greater detail with reference to the accompanying embodiments, it should be noted herein that like elements are denoted by the same reference numerals throughout the disclosure.

Figure 5:
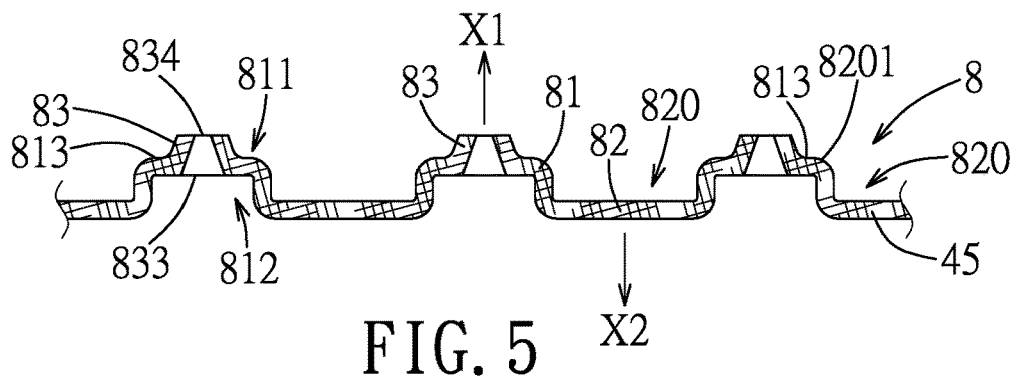
FIG. 5 is a fragmentary sectional view of the first embodiment of the breathable structural web.
Figure 6:
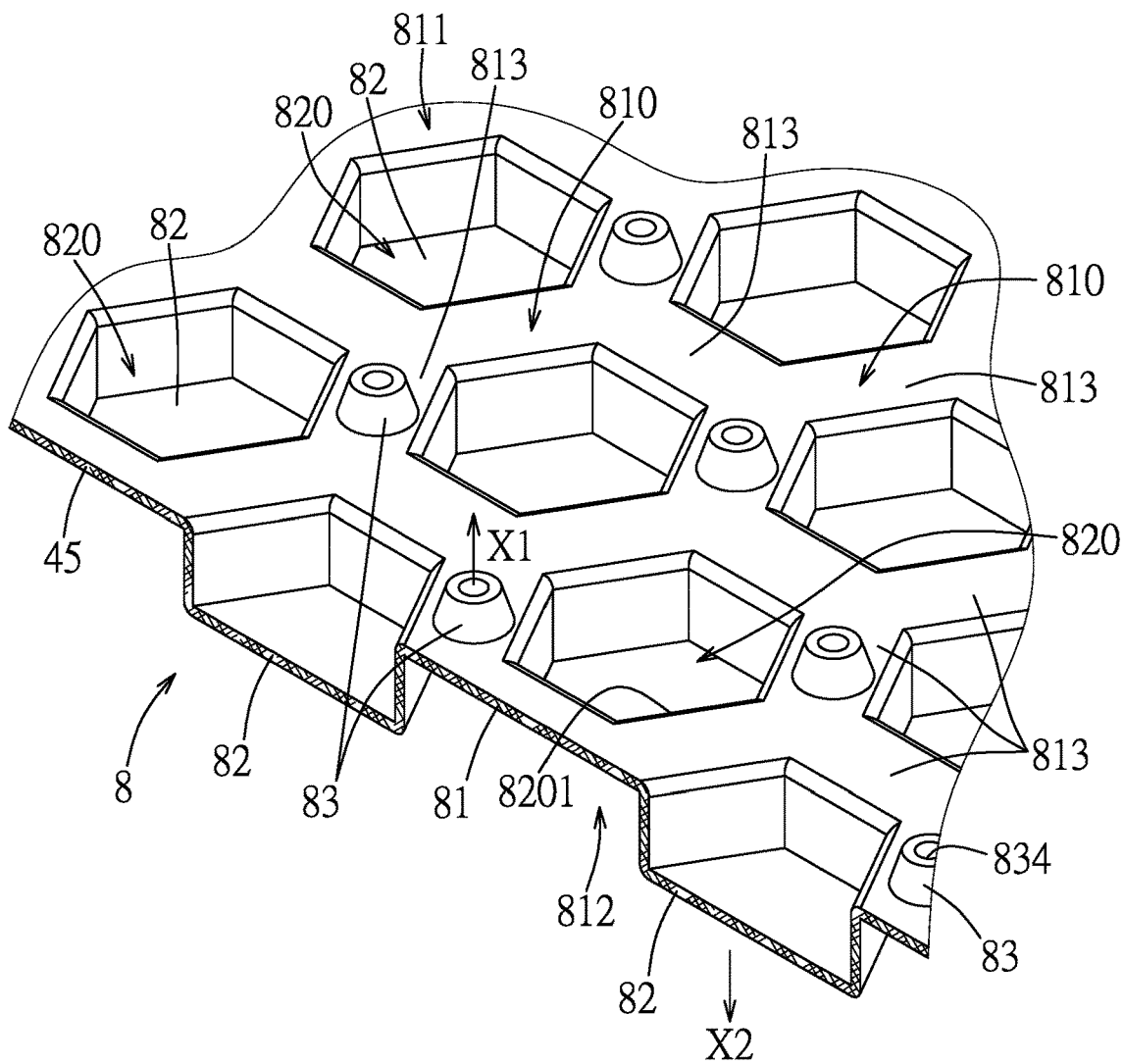
FIG. 6 is a fragmentary perspective view of the first embodiment.

FIGS. 5 and 6 illustrate the first embodiment of a breathable structural web according to the disclosure. The breathable structural web maybe useful in applications, such as diapers, napkins, cloths, filters, etc., and includes a layered structure 8 having at least a first layer 45 of a non-woven material.

The layered structure 8 of the breathable structural web includes a base layer portion 81 that has opposite first and second sides 811, 812, a plurality of first hollow protrusions 83 that are disposed at the first side 811 and that protrude and that are tapered from the base layer portion 81 in a first direction (X1), and a plurality of indented portions 82 that are disposed at the second side 812, that extend from the base layer portion 81 in a second direction (X2) opposite to the first direction (X1), and that respectively define a plurality of recesses 820 which open in the first direction (X1). The first hollow protrusions 83 are scattered among the indented portions 82.

In this embodiment, the base layer portion 81 is formed of a plurality of first ribs 813 that are interconnected to one another to form into a first grid-shaped configuration with a plurality of first grid cells 810. The first hollow protrusions 83 protrude outwardly from the first ribs 813 in the first direction (X1). Each of the recesses 820 has an open end 8201 that is flush with the base layer portion 81. Each of the first grid cells 810 surrounds the open end 8201 of a respective one of the recesses 820.

Each of the first hollow protrusions 83 has a large-diameter open end 833 and a small-diameter open end 834, and further has a diameter that is gradually reduced from the large-diameter open end 833 to the small-diameter open end 834. Preferably, the large-diameter open end 833 has a diameter ranging from greater than 5 μm to 100 μm, and the small-diameter open end 834 has a diameter ranging from 0.1 μm to 10 μm. More preferably, the large-diameter open end 833 has a diameter ranging from greater than 10 μm to 50 μm, and the small-diameter open end 834 has a diameter ranging from 0.5 μm to 5 μm.

Figure 2:
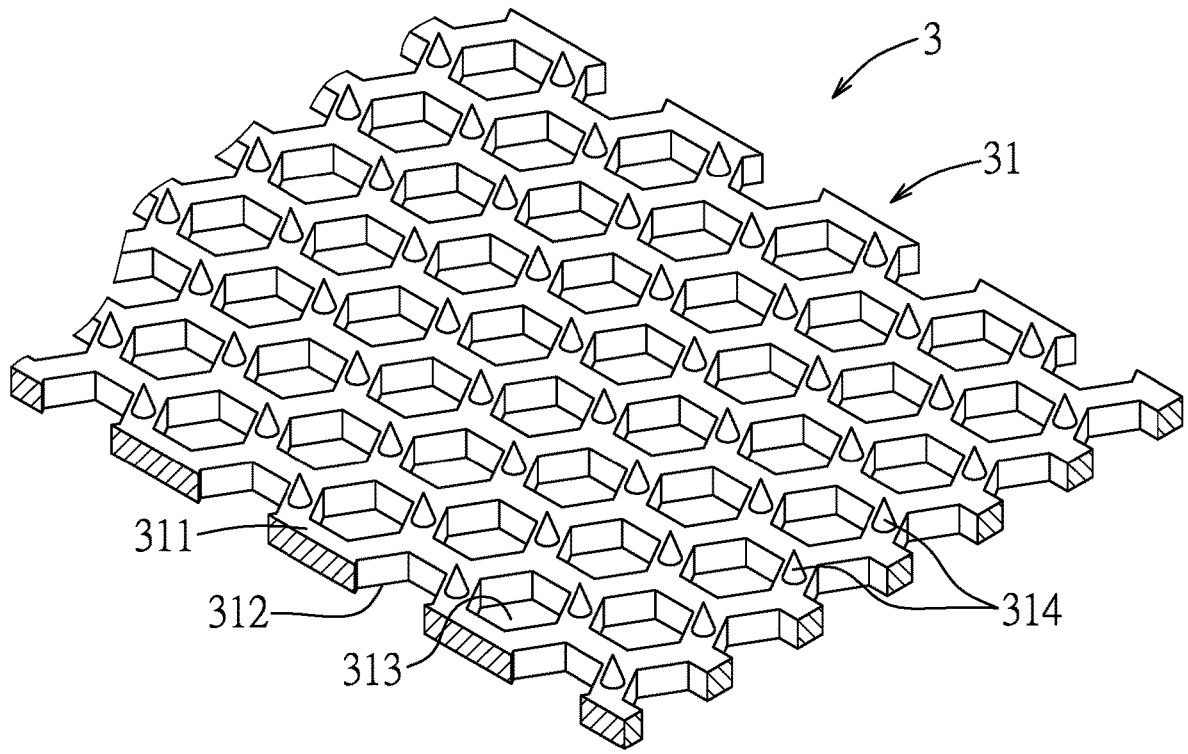
FIG. 2 is a perspective view of a screen mold of the breathable structural web-forming apparatus used for making the first embodiment.
Figure 3:
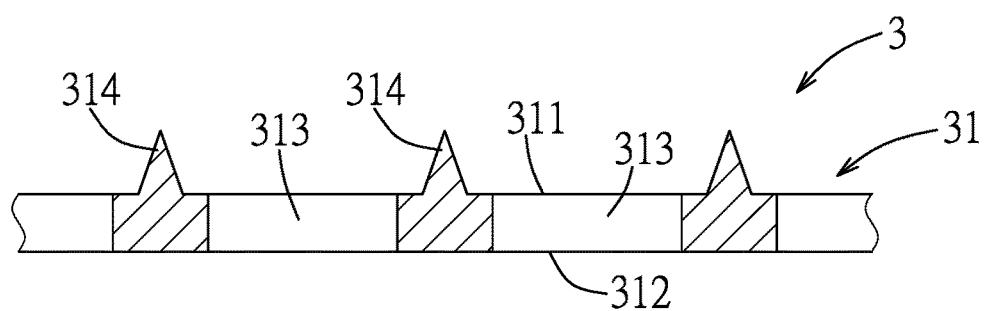
FIG. 3 is a fragmentary sectional view of the screen mold of FIG. 2.

FIGS. 1 to 3 illustrate an example of a breathable structural web-forming apparatus for forming the first embodiment of the breathable structural web according to the disclosure. The breathable structural web-forming apparatus includes: a first rotary member 22 with a first shaft 21 defining a first rotation axis (X) and rotatable about the first rotation axis (X); a second rotary member 24 with a second shaft 23 defining a second rotation axis (Y) and rotatable about the second rotation axis (Y); a first screen mold 3 supported and trained on the first and second rotary members 22, 24 and co-rotatable with the first and second rotary members 22, 24, the first screen mold 3 including a first screen body 31 and a plurality of first tapered projections 314, the first screen body 31 having first and second sides 311, 312, and a plurality of first screen holes 313, the first tapered projections 314 protruding and being tapered from the first side 311 of the first screen body 31, the first and second axes (X, Y) being parallel to each other, the first and second rotary members 22, 24 being spaced apart from each other; a first extruder 41 for melting pellets of a polymeric material 43 and extruding a melt of the polymeric material 43; a spinneret 42 that is connected to the first extruder 41 for receiving the melt of the polymeric material 43 from the first extruder 41, that is disposed adjacent to the first side 311 of the first screen body 31 opposite to the second side 312 of the first screen body 31, and that is configured to discharge molten fibers 44 toward the first side 311 of the first screen body 31 for forming the first layer 45 of the non-woven material; a heater 6 disposed adjacent to the spinneret 42 for maintaining the molten fibers 44 under the melting state on the first screen mold 3; and a suction box 5 that is disposed adjacent to the second side 312 of the first screen body 31 opposite to the first side 311 of the first screen body 31 between the first and second rotary members 22, 24, and that is configured to draw the molten fibers 44 to fit into the first screen holes 313, thereby forming the layered structure 8 of the breathable structural web.

Preferably, the polymeric material 43 is selected from the group consisting of polyester, polyolefin, polyurethane, polyamide, and other commercial resins suitable for making the nonwoven material.

Figure 4:
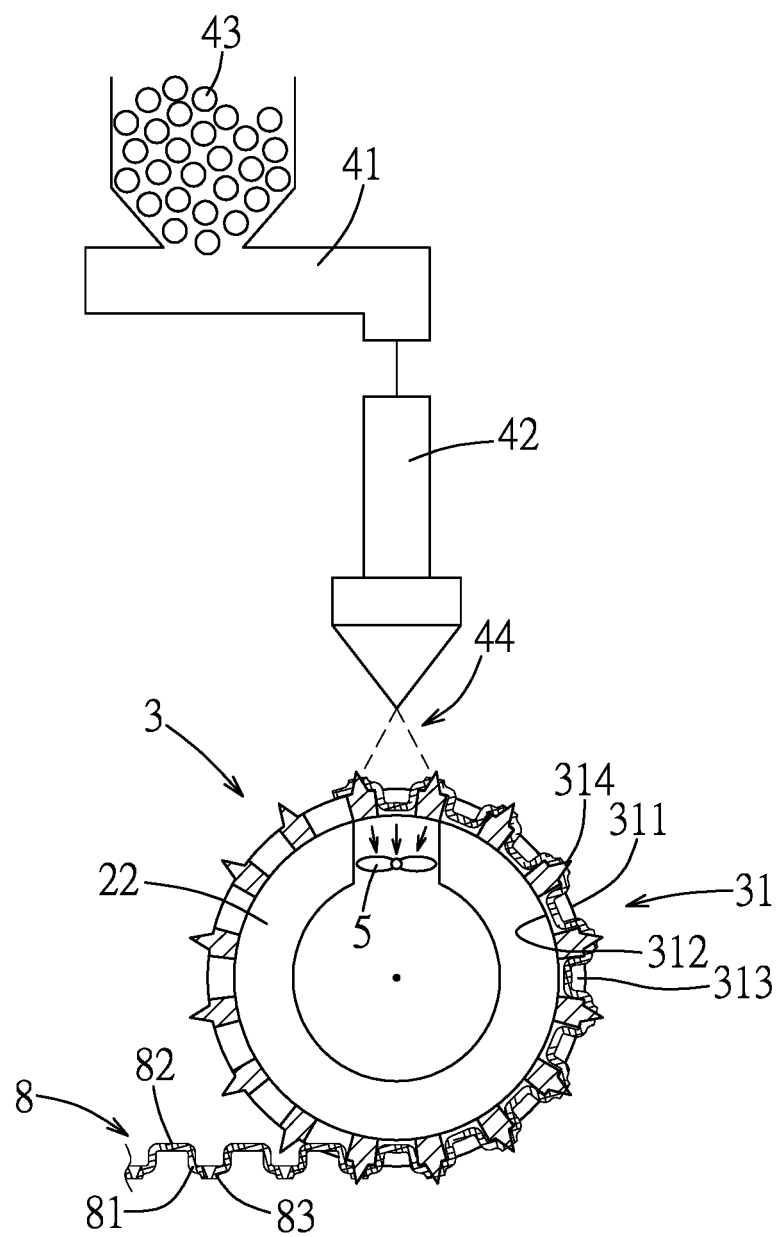
FIG. 4 is a schematic view of another breathable structural web-forming apparatus used for making the first embodiment.

FIG. 4 illustrates another example of the breathable structural web-forming apparatus for forming the first embodiment of the breathable structural web according to the disclosure. The breathable structural web-forming apparatus of FIG. 4 differs from that of FIG. 1 in that the second rotary member 24 is dispensed with and that the first screen mold 3 is trained on the first rotary member 22 (which is in the form of a cylindrical rotary drum) with the suction box 5 being disposed in the first rotary member 22.

Figure 9:
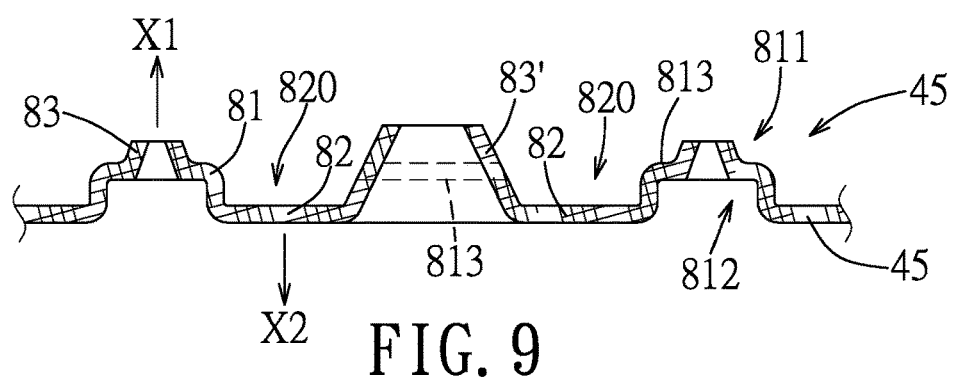
FIG. 9 is a fragmentary sectional view of the second embodiment of the breathable structural web.

FIG. 9 illustrates the second embodiment of the breathable structural web according to the disclosure. The second embodiment differs from the first embodiment in that the layered structure 8 further includes a plurality of second hollow protrusions 83', each of which protrudes and is tapered from a respective one of the first ribs 813 and two adjacent ones of the indented portions 82 in the first direction (X1).

Figure 7:
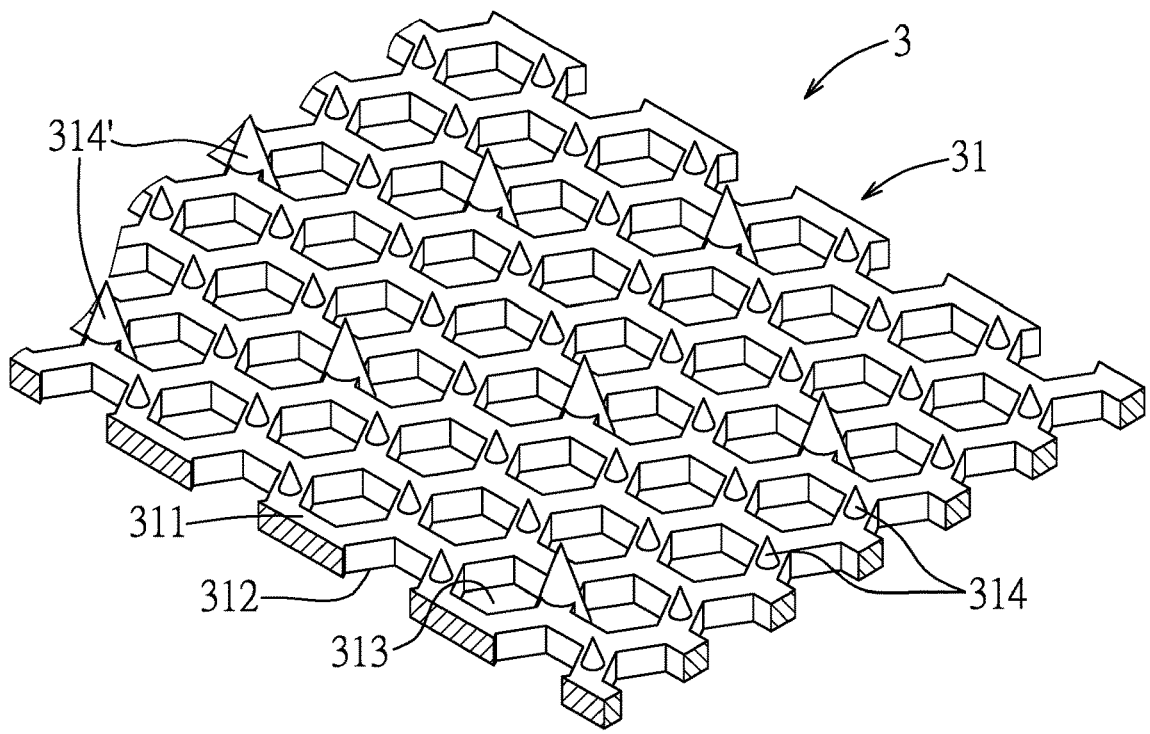
FIG. 7 is a fragmentary perspective view of a screen mold used for making the second embodiment of the breathable structural web according to the disclosure.
Figure 8:
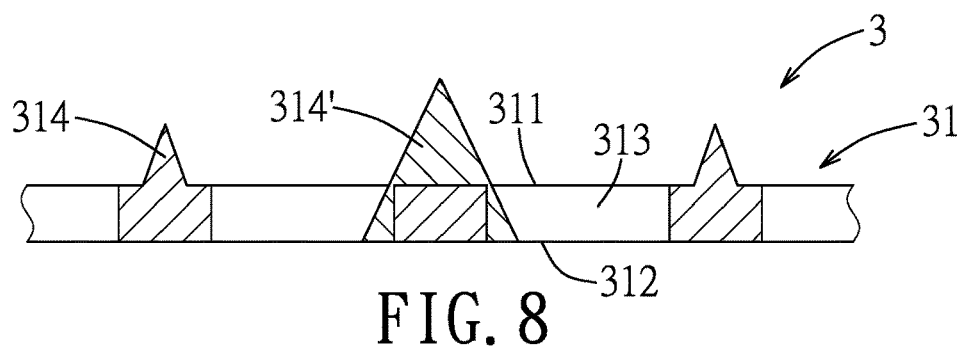
FIG. 8 is a fragmentary sectional view of the screen mold used for making the second embodiment.

FIGS. 7 and 8 illustrate a modified first screen mold 3 used in the breathable structural web-forming apparatus for forming the second embodiment of the breathable structural web according to the disclosure. The modified first screen mold 3 of FIG. 7 differs from the first screen mold 3 of FIG. 2 in that the modified first screen mold 3 of FIG. 7 further includes a plurality of conical protuberances 314' that extend and that are tapered from the second side 312 of the first screen body 31 beyond the first side 311 of the first screen body 31.

Figure 13:
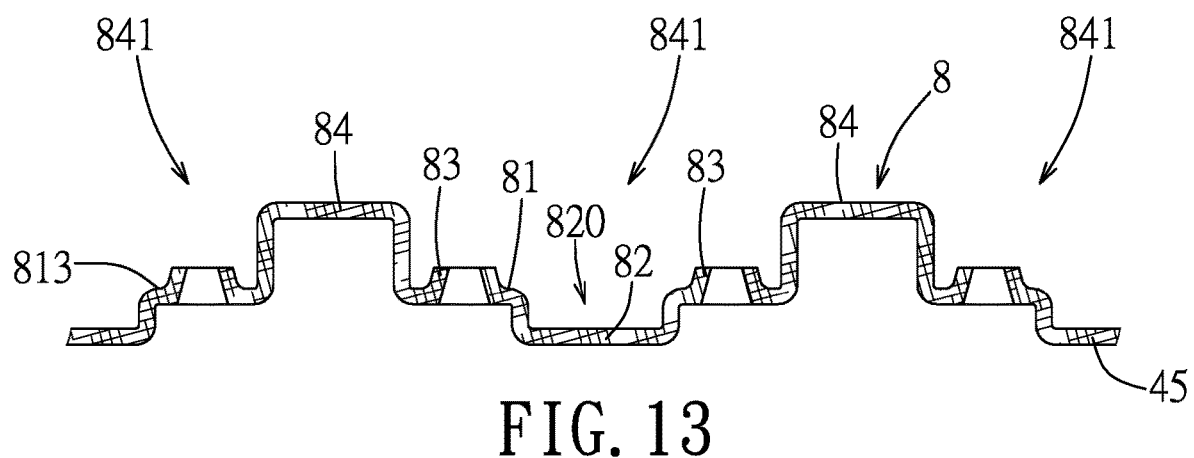
FIG. 13 is a fragmentary sectional view of the third embodiment of the breathable structural web.
Figure 14:
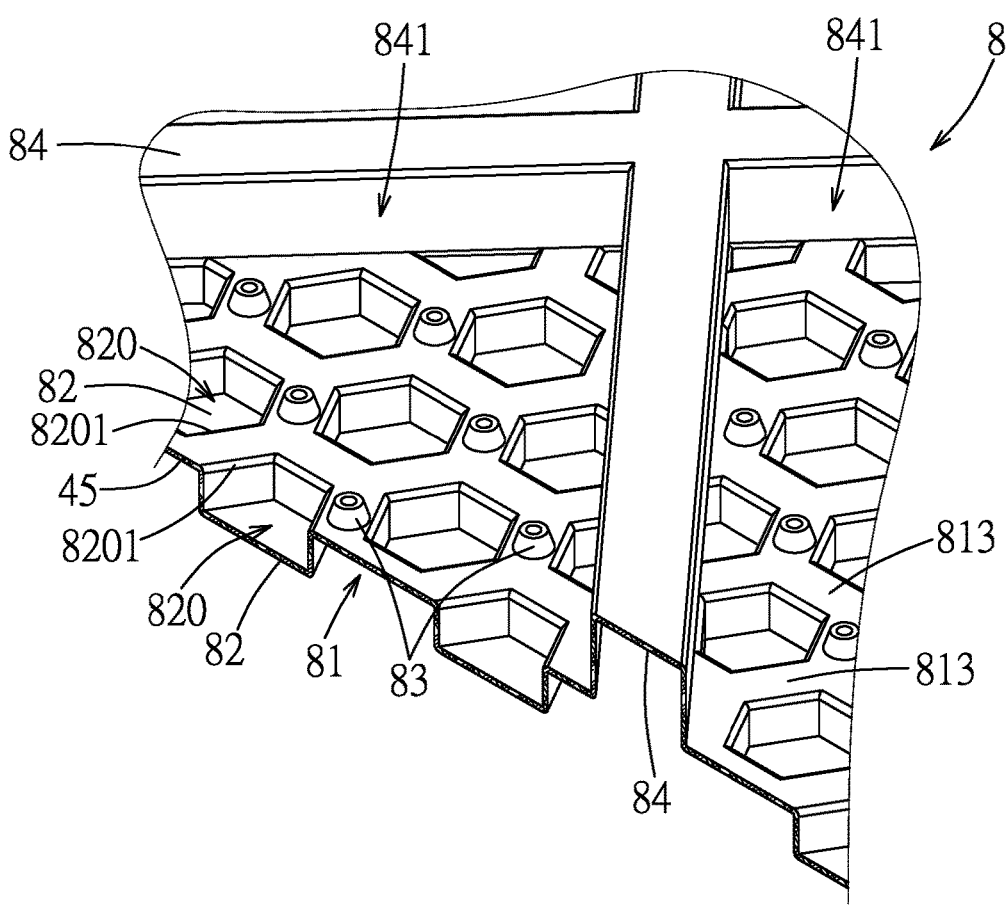
FIG. 14 is a fragmentary perspective view of the third embodiment.

FIGS. 13 and 14 illustrate the third embodiment of the breathable structural web according to the disclosure. The third embodiment differs from the first embodiment in that the layered structure 8 further includes a plurality of second ribs 84 that are interconnected to one another to form into a second grid-shaped configuration with a plurality of second grid cells 841, and that protrude from the base layer portion 81 in the first direction (X1). Each of the second grid cells 841 surrounds respective ones of the first hollow protrusions 83 and respective ones of the open ends 8201 of the recesses 820.

Figure 10:
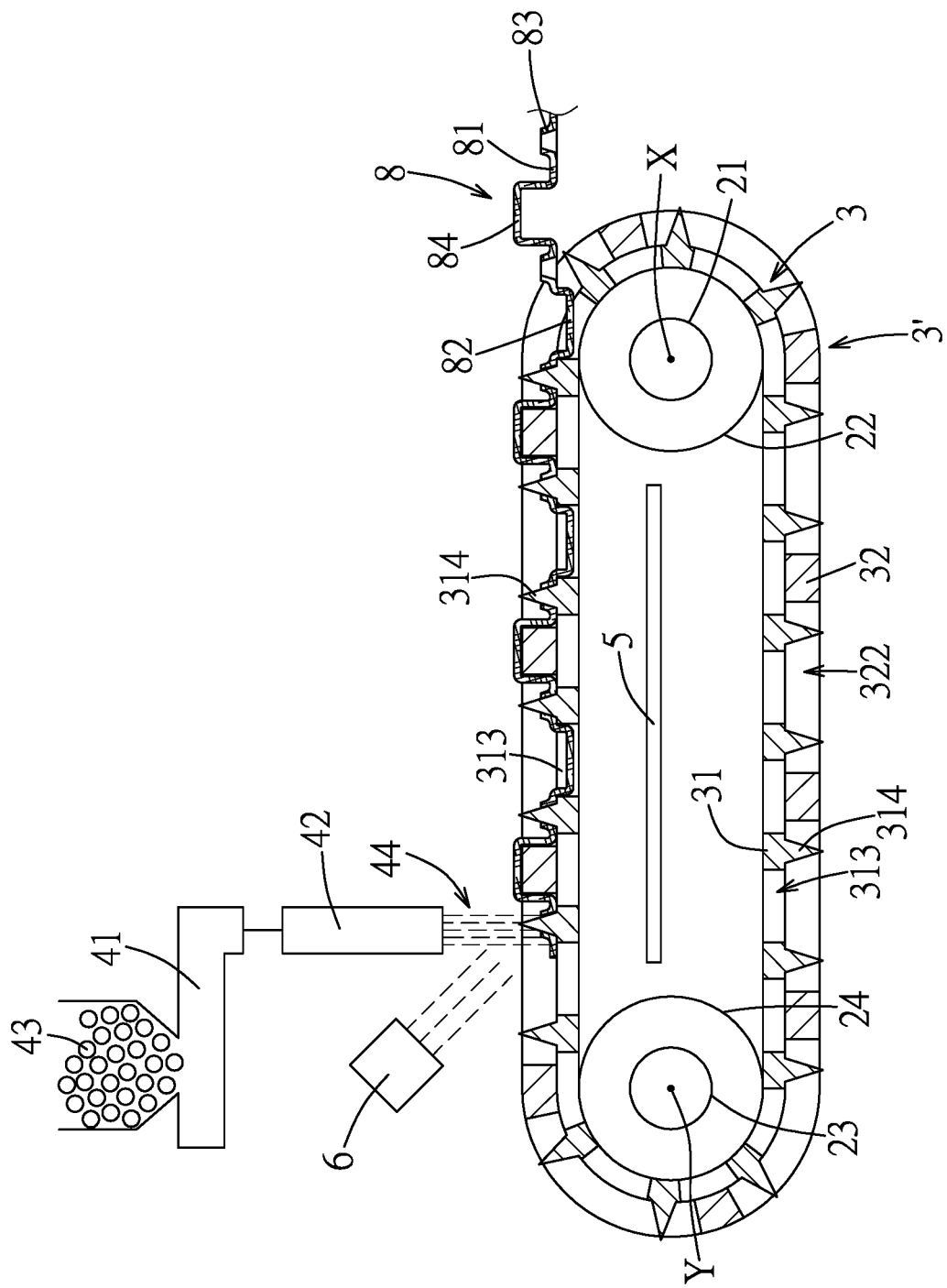
FIG. 10 is a schematic view of a breathable structural web-forming apparatus used for making the third embodiment of the breathable structural web according to the disclosure.
Figure 11:
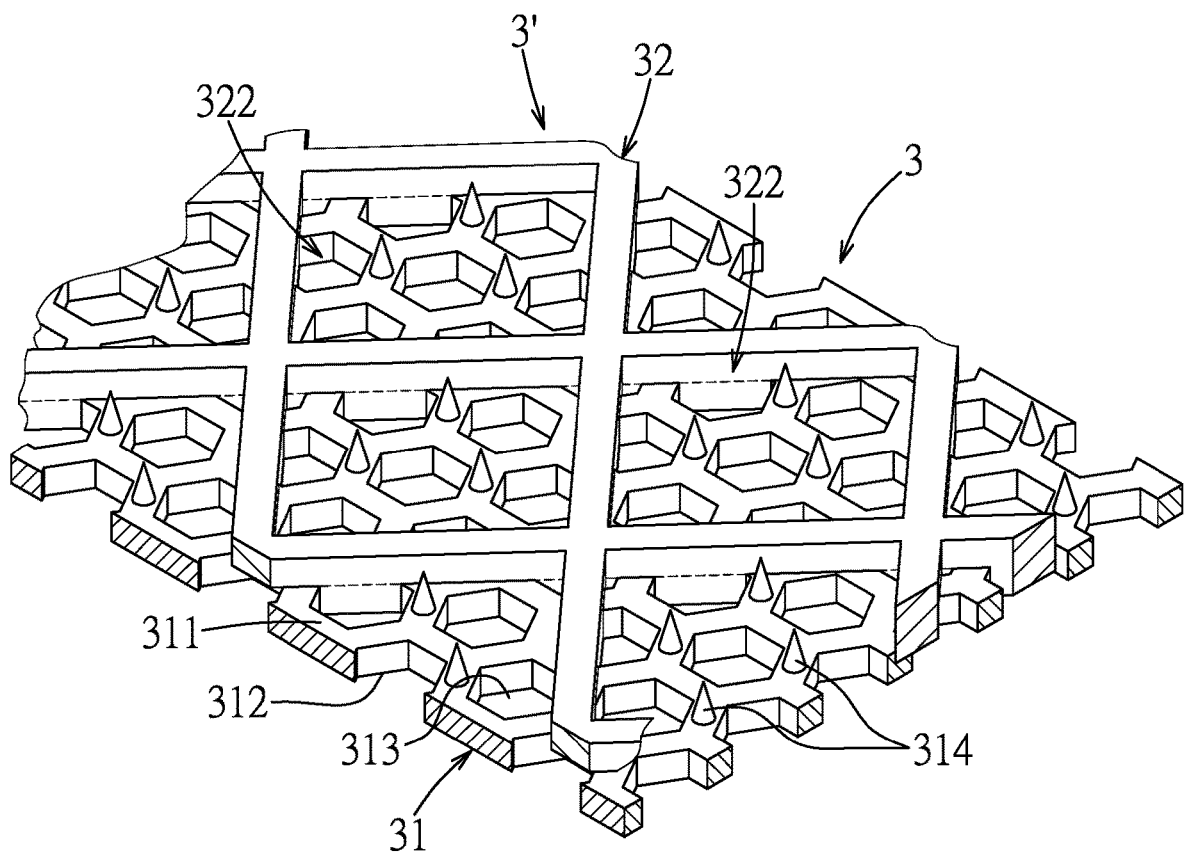
FIG. 11 is a perspective view of a screen mold of the breathable structural web-forming apparatus used for making the third embodiment.
Figure 12:
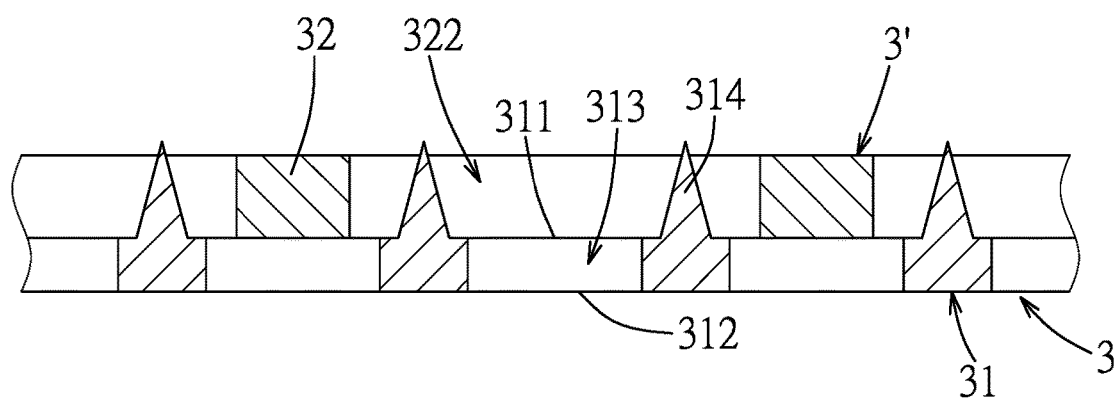
FIG. 12 is a fragmentary sectional view of the screen mold of FIG. 11.

FIGS. 10 to 12 illustrate the breathable structural web-forming apparatus for forming the third embodiment of the breathable structural web according to the disclosure. The breathable structural web-forming apparatus of FIGS. 10 to 12 differs from that of FIGS. 1 to 3 in that the breathable structural web-forming apparatus of FIGS. 10 to 12 further includes a second screen mold 3' having a second screen body 32 that is stacked on the first screen body 31 of the first screen mold 3 and that defines a plurality of second screen hole 322. Each of the second screen holes 322 has an area larger than that of each of the first screen holes 313.

Figure 17:
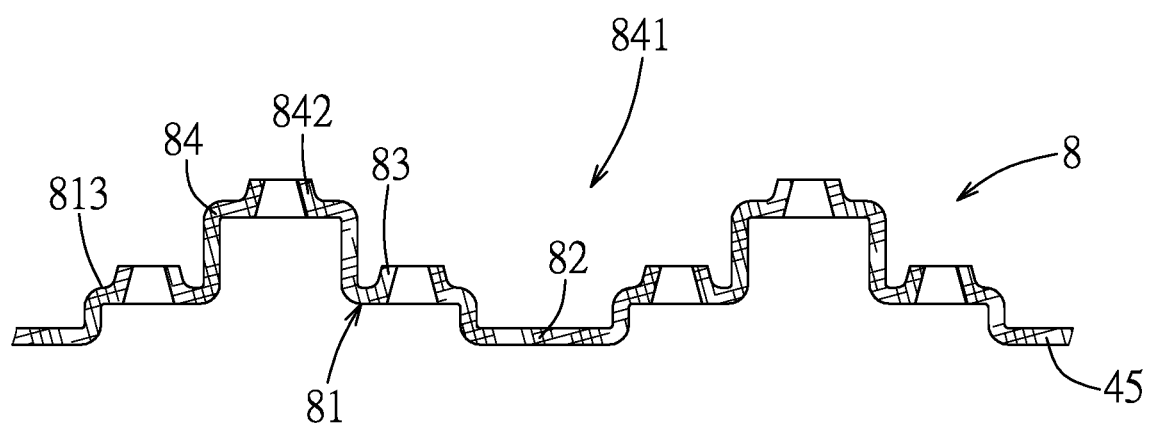
FIG. 17 is a fragmentary sectional view of the fourth embodiment of the breathable structural web.

FIG. 17 illustrates the fourth embodiment of the breathable structural web according to the disclosure. The fourth embodiment differs from the third embodiment in that the layered structure 8 further includes a plurality of hollow studs 842 that protrude and are tapered from the second ribs 84 in the first direction (X1).

Figure 15:
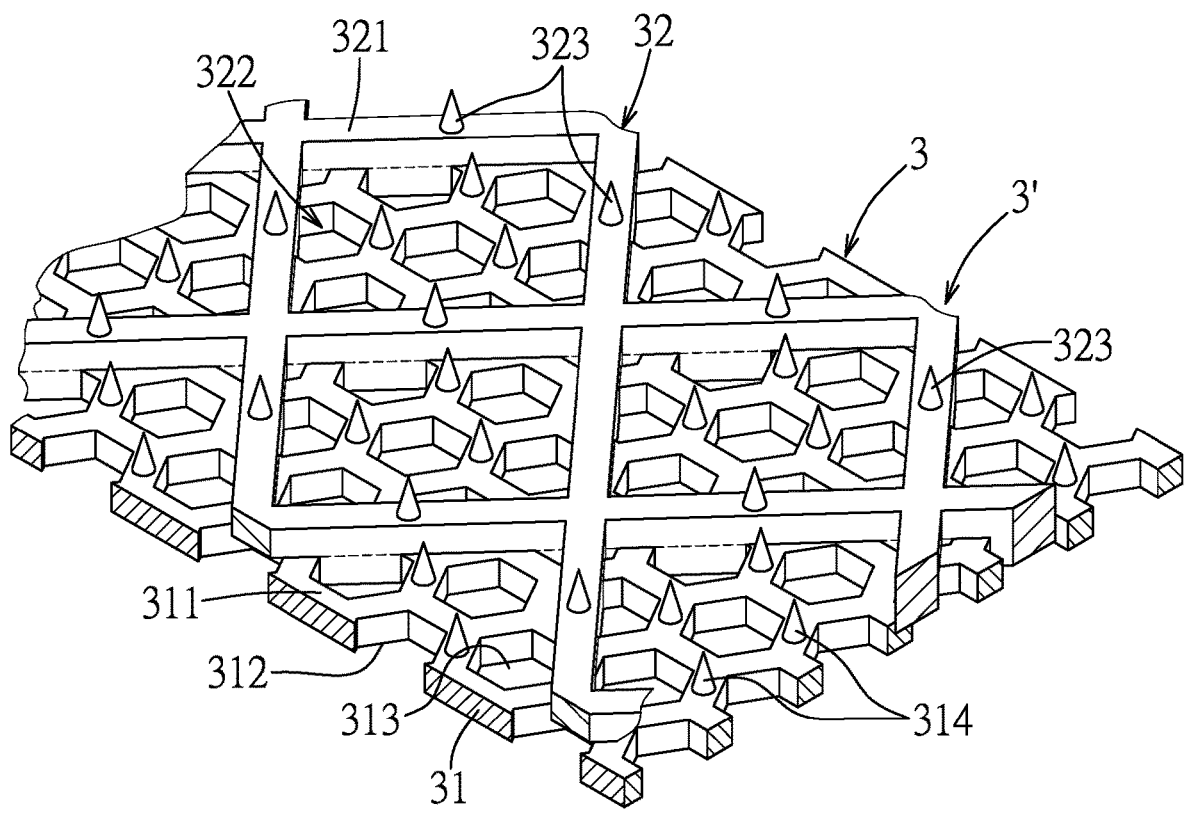
FIG. 15 is a fragmentary perspective view of a screen mold used for making the fourth embodiment of the breathable structural web according to the disclosure.
Figure 16:
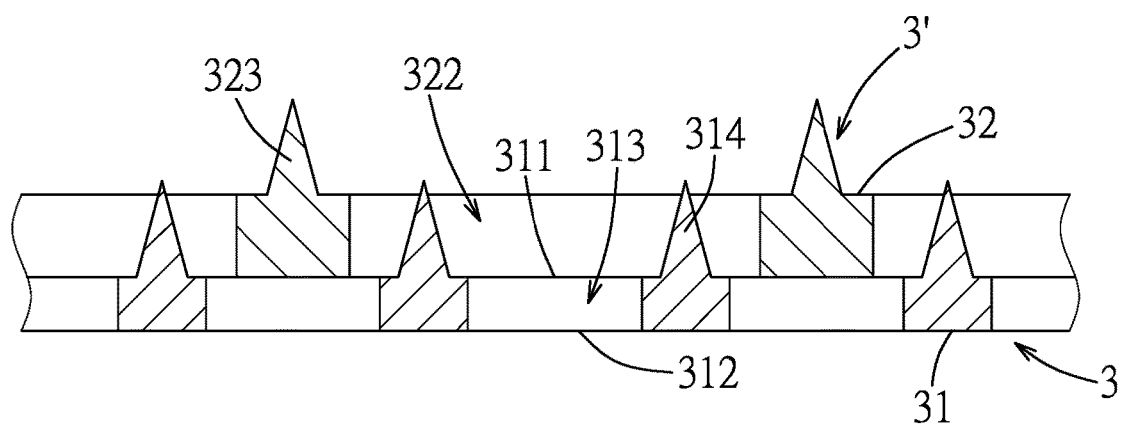
FIG. 16 is a fragmentary sectional view of the screen mold used for making the fourth embodiment.

FIGS. 15 and 16 illustrate the breathable structural web-forming apparatus for forming the fourth embodiment of the breathable structural web according to the disclosure. The breathable structural web-forming apparatus of FIGS. 15 and 16 differs from that of FIGS. 10 to 12 in that the second screen mold 3' of the breathable structural web-forming apparatus of FIGS. 15 and 16 further includes a plurality of second tapered projections 323 that protrude and are tapered from the second screen body 32.

Figure 19:
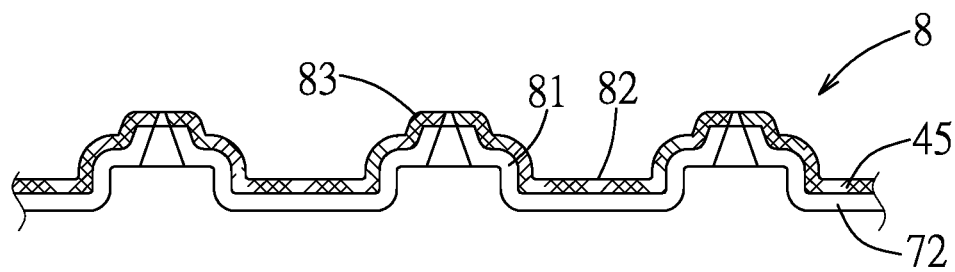
FIG. 19 is a fragmentary sectional view of the fifth embodiment of the breathable structural web.
Figure 20:
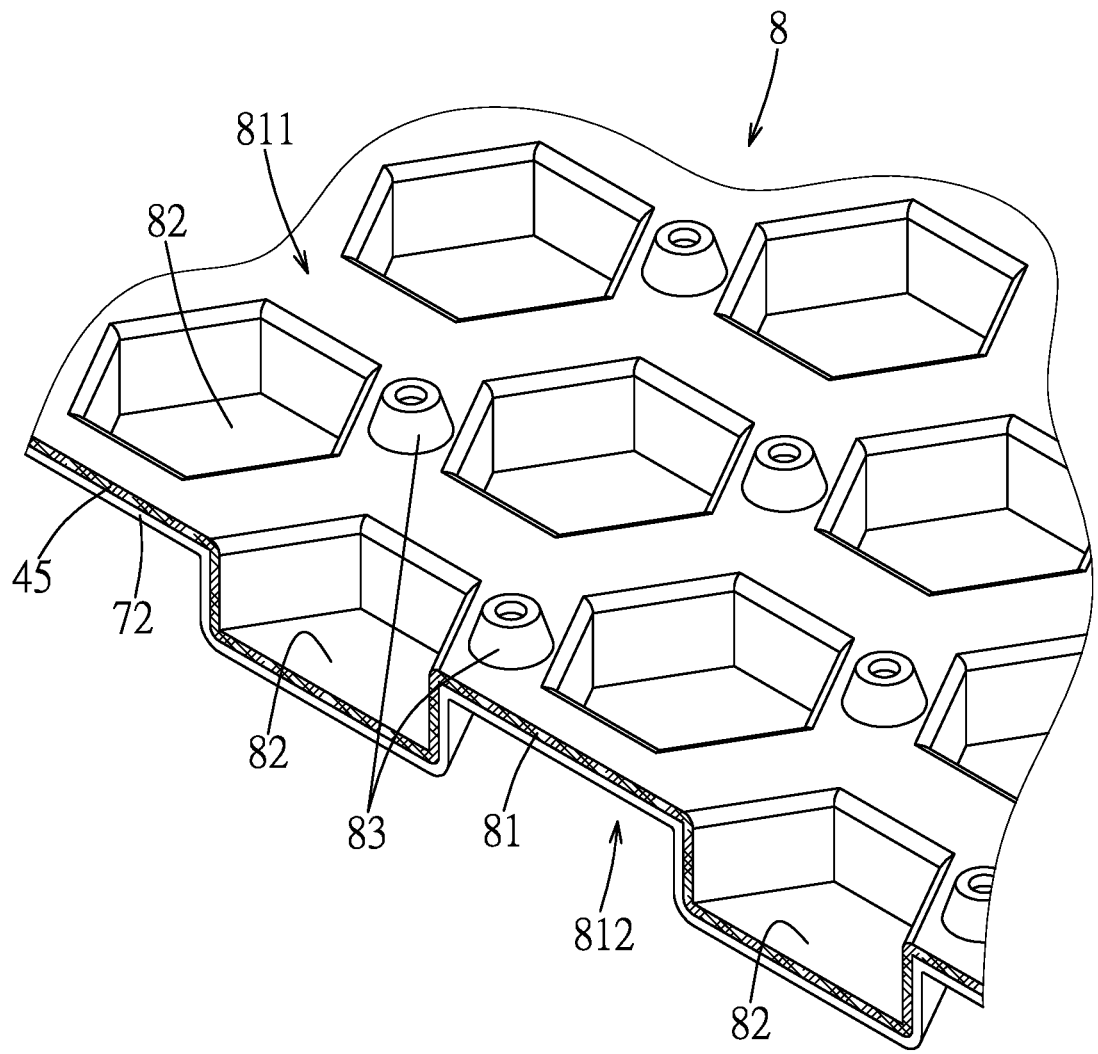
FIG. 20 is a fragmentary perspective view of the fifth embodiment.

FIGS. 19 and 20 illustrate the fifth embodiment of the breathable structural web according to the disclosure. The fifth embodiment differs from the first embodiment in that the layered structure 8 further includes a second layer 72 of a plastic film that is stacked on and that is bonded to the first layer 45. The second layer 72 is disposed at one side of the first layer 45, while the first hollow protrusions 83 are disposed at an opposite side of the first layer 45.

Preferably, the plastic film is a waterproof film, and is made from a plastic material selected from the group consisting of polyester, polyolefin, and other commercial resins suitable for making the plastic film.

Figure 18:
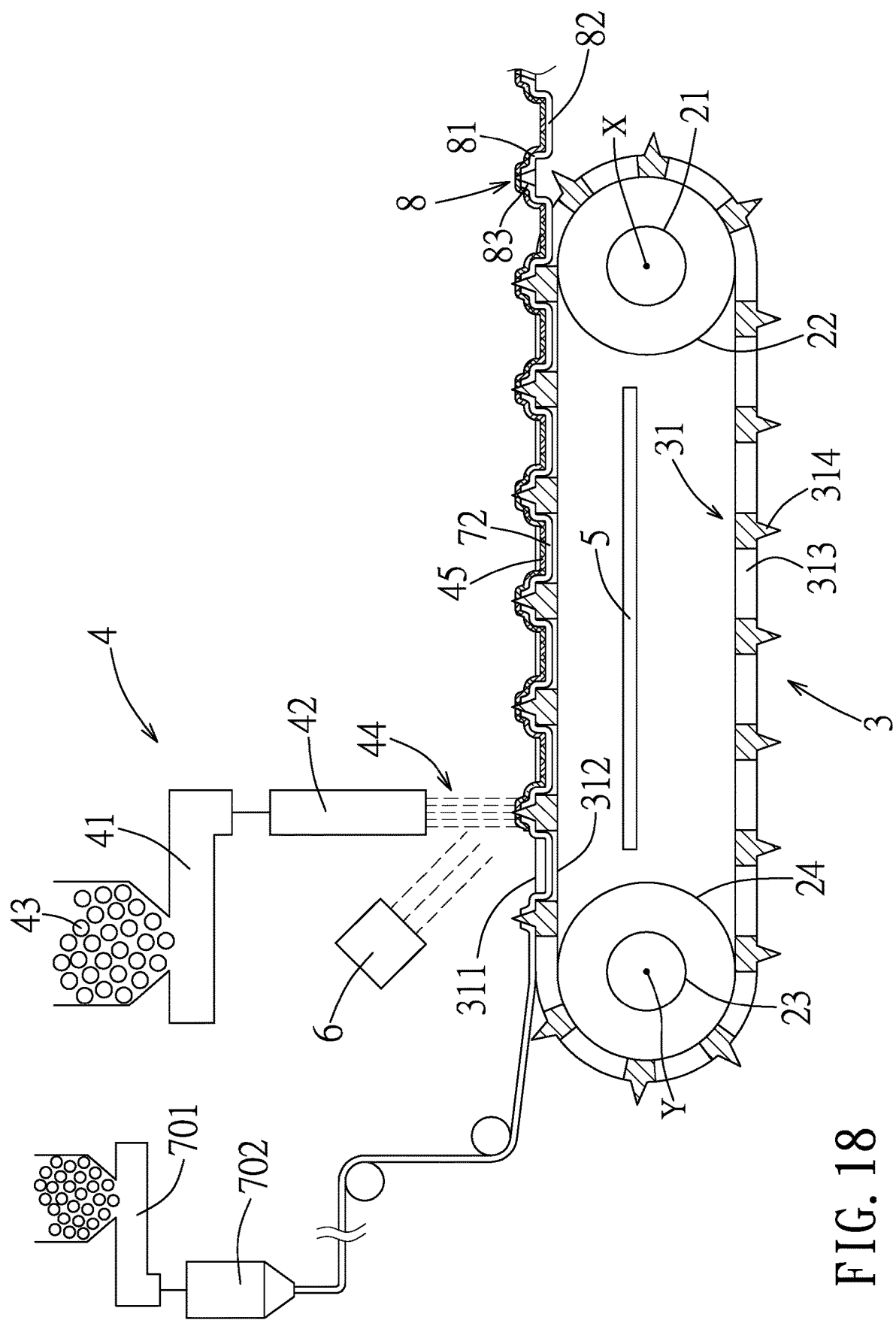
FIG. 18 is a schematic view of a breathable structural web-forming apparatus used for making the fifth embodiment of the breathable structural web according to the disclosure.

FIG. 18 illustrates the breathable structural web-forming apparatus for forming the fifth embodiment of the breathable structural web according to the disclosure. The breathable structural web-forming apparatus of FIG. 18 differs from that of FIGS. 1 in that the breathable structural web-forming apparatus of FIG. 18 further includes a second extruder 701 for melting and discharging a plastic material, and a film-forming member 702 that is disposed adjacent to the second extruder to receive and shape the melted plastic material into a plastic film, and that is further disposed adjacent to the first side 311 of the first screen body 31 and that is configured to discharge the plastic film onto the first side 311 of the first screen body 31 at an upstream of the spinneret 42, such that the molten fibers 44 discharged from the spinneret 42 are laid on the plastic film on the first side 311 of the first screen body 31, thereby forming the breathable structural web of the fifth embodiment.

Figure 22:
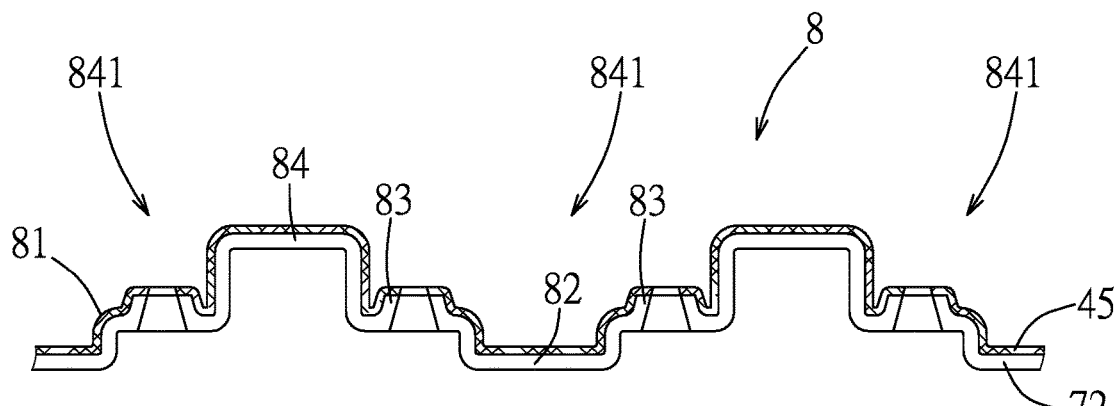
FIG. 22 is a fragmentary sectional view of the sixth embodiment of the breathable structural web.
Figure 23:
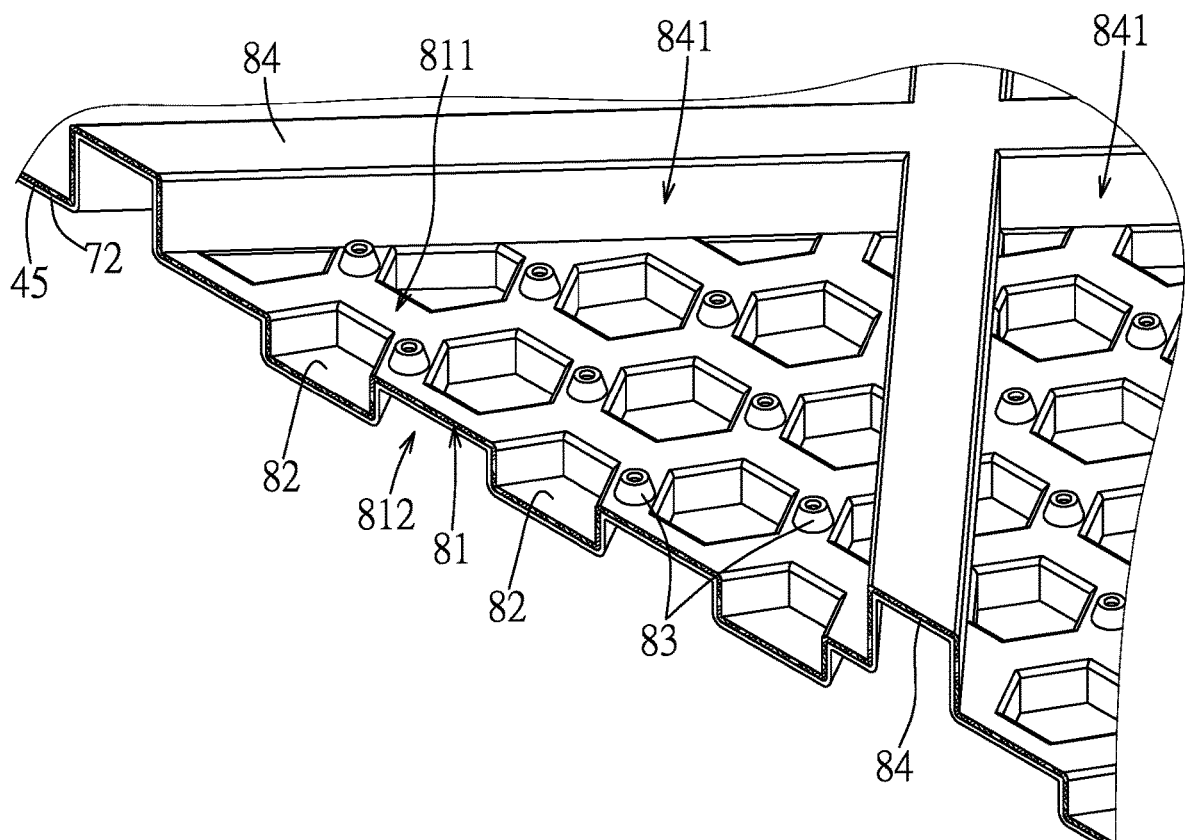
FIG. 23 is a fragmentary perspective view of the sixth embodiment.

FIGS. 22 and 23 illustrate the sixth embodiment of the breathable structural web according to the disclosure. The sixth embodiment differs from the third embodiment in that the layered structure 8 further includes a second layer 72 of a plastic film that is stacked on and that is bonded to the first layer 45. The second layer 72 is disposed at one side of the first layer 45, while the first hollow protrusions 83 are disposed at an opposite side of the first layer 45.

Figure 21:
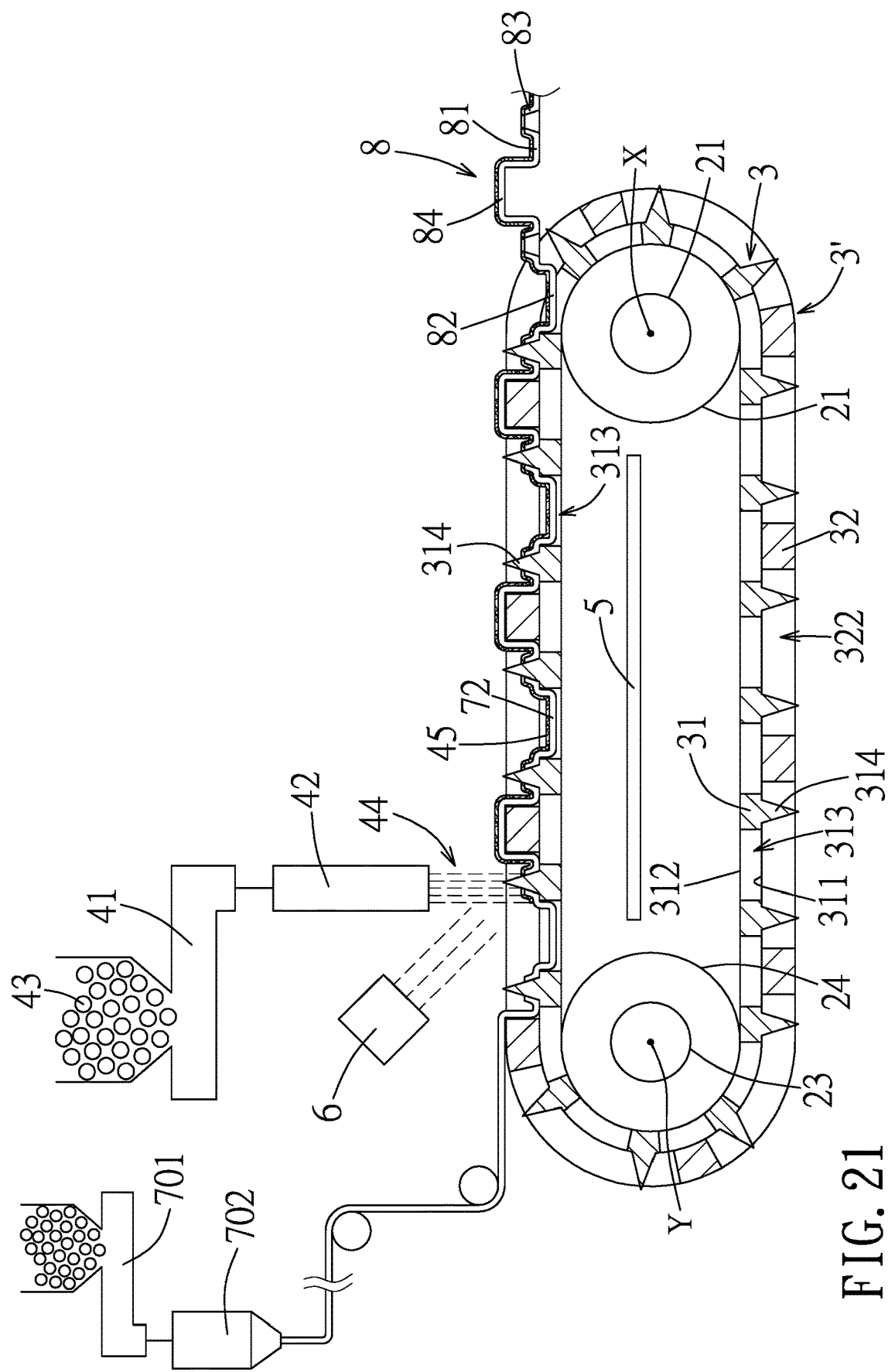
FIG. 21 is a schematic view of a breathable structural web-forming apparatus used for making the sixth embodiment of the breathable structural web according to the disclosure.

FIG. 21 illustrates the breathable structural web-forming apparatus for forming the sixth embodiment of the breathable structural web according to the disclosure. The breathable structural web-forming apparatus of FIG. 21 differs from that of FIGS. 10 in that the breathable structural web-forming apparatus of FIG. 21 further includes a second extruder 701 for melting and discharging a plastic material, and a film-forming member 702 that is disposed adjacent to the second extruder to receive and shape the melted plastic material into a plastic film, and that is further disposed adjacent to the first side 311 of the first screen body 31 and that is configured to discharge the plastic film onto the first side 311 of the first screen body 31 at an upstream of the spinneret 42, such that the molten fibers 44 discharged from the spinneret 42 are laid on the plastic film on the first side 311 of the first screen body 31, thereby forming the breathable structural web of the sixth embodiment.

The advantages of the breathable structural web of the disclosure may be better illustrated in the following applications.

Figure 24:
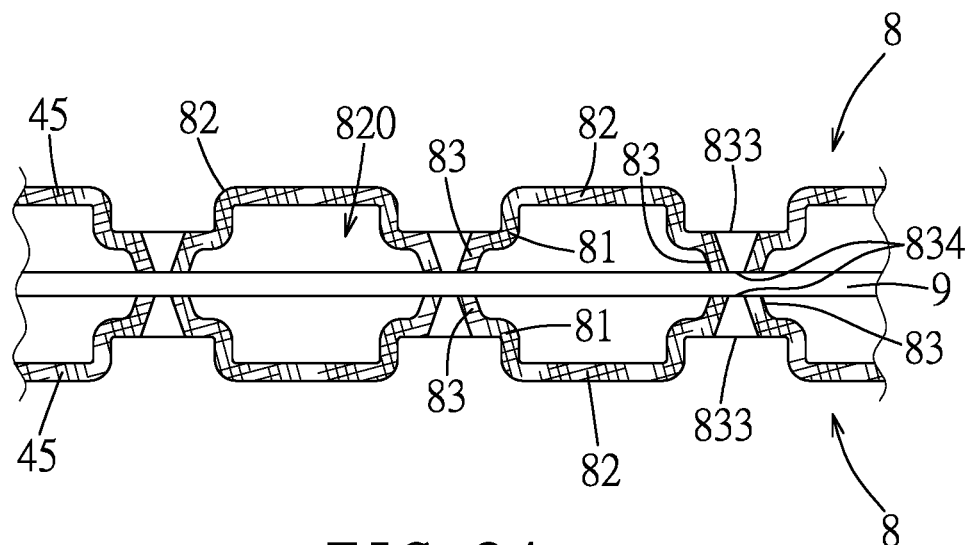
FIG. 24 is a fragmentary sectional view of a diaper including two layered structures of the first embodiment of the breathable structural web.

FIG. 24 illustrates an application of the breathable structural web according to the disclosure in a diaper. The diaper includes first and second breathable structural webs and an absorbent 9. Each of the first and second breathable structural webs has a layered structure 8 the same as that of the first embodiment. The absorbent 9 is stacked on and is sandwiched between the layered structures 8 of the first and second breathable structural webs. Each of the first hollow protrusions 83 of the layered structure 8 of the first breathable structural web is aligned with a respective one of the first hollow protrusions 83 of the layered structure 8 of the second breathable structural web along a normal direction normal to the first and second breathable structural webs. The small-diameter open ends 834 of the first hollow protrusions 83 of the layered structures 8 of the first breathable structural web are in contact with one side of the absorbent 9 and the small-diameter open ends 834 of the first hollow protrusions 83 of the layered structures 8 of the second breathable structural web are in contact with the other side of the absorbent 9 that is opposite to the one side of the absorbent. The indented portions 82 of the layered structure 8 of the first breathable structural web are to be brought into contact with the skin of the user. As such, the base layer portion 81 of the layered structure 8 of the first breathable structural web is spaced apart from (i.e., free from contact with) the skin of the user by the indented portions of the layered structure 8 of the first breathable structural web, thereby permitting reduction of the contact area between the diaper and the skin of the user. The first hollow protrusions 83 of the layered structure 8 have a gradually reduced diameter, so that air and/or vapor are permitted to pass therethrough while liquid is prevented from passing therethrough, thereby keeping the user in a dry and comfortable state. It is noted that during urination, urine may pass through pores in the layered structure 8 of the first breathable structural web, is absorbed by the absorbent 9, and is prevented from re-wetting the skin of the user by passing through the base layer portion 81, the first hollow protrusions 83 and the indented portions 82 of the layered structure 8 of the first breathable structural web.

Figure 25:
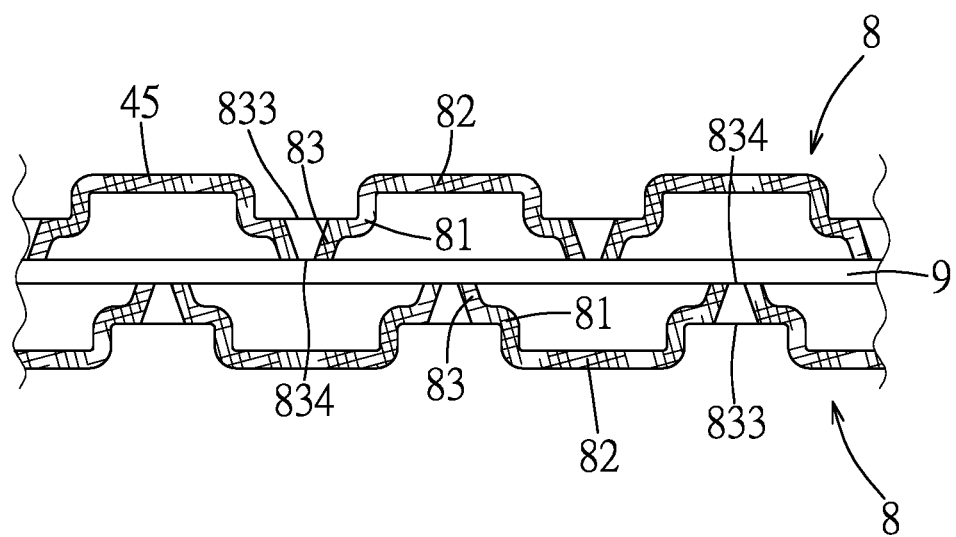
FIG. 25 is a fragmentary sectional view of another diaper modified from the diaper of FIG. 24.

FIG. 25 illustrates a diaper modified from the diaper of FIG. 24. The diaper of FIG. 25 differs from the diaper of FIG. 24 in that each of the first hollow protrusions 83 of the layered structure 8 of the first breathable structural web is misaligned with the respective one of the first hollow protrusions 83 of the layered structure 8 of the second breathable structural web along the normal direction.

While the disclosure has been described in connection with what are considered the practical embodiments, it is understood that the disclosure is not limited to the disclosed embodiments but is intended to cover various arrangements included within the spirit and scope of the broadest interpretation and equivalent arrangements.

What is claimed is:

1. A breathable structural web comprising:
a layered structure that includes at least a first layer of a non-woven material, said layered structure including:
a base layer portion that has opposite first and second sides, said base layer portion formed of a plurality of first ribs that are interconnected to one another to form into a first grid-shaped configuration with a plurality of first grid cells,
a plurality of first hollow protrusions that are disposed at said first side and that protrude and that are tapered from said base layer portion in a first direction,
a plurality of indented portions that are disposed at said second side, that extend from said base layer portion in a second direction opposite to the first direction, and that respectively define a plurality of recesses which open in the first direction, said first hollow protrusions being scattered among said indented portions, and said first hollow protrusions directly protruding outwardly from said first ribs in the first direction, and
a plurality of second hollow protrusions different in size from said plurality of first hollow protrusions, wherein each of said plurality of second hollow protrusions directly protrudes and is tapered in the first direction from each of two adjacent ones of said indented portions and from a respective one of said first ribs located between said two adjacent ones of said indented portions.

2. The breathable structural web of claim 1, wherein each of said recesses has an open end that is flush with said base layer portion, and each of said first grid cells surrounds said open end of a respective one of said recesses.

3. The breathable structural web of claim 2, wherein said layered structure further includes a plurality of second ribs that are interconnected to one another to form into a second grid-shaped configuration with a plurality of second grid cells, and that protrude from said base layer portion in the first direction, each of said second grid cells surrounding respective ones of said first hollow protrusions and respective ones of said open ends of said recesses.

4. The breathable structural web of claim 3, wherein said layered structure further includes a plurality of hollow studs that protrude and are tapered from said second ribs in the first direction.

5. The breathable structural web of claim 1, wherein said layered structure further includes a second layer of a plastic film that is stacked on and that is bonded to said first layer.

6. A breathable diaper comprising:
a first breathable structural web; and
an absorbent stacked on said first breathable structural web;
wherein said first breathable structural web includes a layered structure having at least a first layer of a non-woven material, said layered structure including:
a base layer portion that has opposite first and second sides, said base layer portion is formed of a plurality of first ribs that are interconnected to one another to form into a first grid-shaped configuration with a plurality of first grid cells,
a plurality of first hollow protrusions that are disposed at said first side and that protrude and that are tapered from said base layer portion in a first direction, and
a plurality of indented portions that are disposed at said second side, that extend from said base layer portion in a second direction opposite to the first direction, and that respectively define a plurality of recesses which open in the first direction, said first hollow protrusions being scattered among said indented portions, and said first hollow protrusions directly protruding outwardly from said first ribs in the first direction, and
a plurality of second hollow protrusions different in size from said plurality of first hollow protrusions, wherein each of said plurality of second hollow protrusions directly protrudes and is tapered in the first direction from each of two adjacent ones of said indented portions and from a respective one of said first ribs located between said two adjacent ones of said indented portions.

7. The breathable diaper of claim 6, further comprising a second breathable structural web, said absorbent being sandwiched between said first and second breathable structural webs, said first and second webs having the same structure.

8. The breathable diaper of claim 7, wherein said first hollow protrusions of said layered structure of said first breathable structural web contact one side of said absorbent, and said first hollow protrusions of said layered structure of said second breathable structural web contact the other side of said absorbent that is opposite to said one side of said absorbent.

9. The breathable diaper of claim 6, wherein said layered structure further includes a second layer of a plastic film that is stacked on and that is bonded to said first layer.

10. The breathable structural web of claim 1, wherein said plurality of second hollow protrusions each has a height extending in the first direction that is longer than a height of any one of said first hollow protrusions.

11. The breathable structural web of claim 1, wherein said plurality of second hollow protrusions each extends farther away from said base layer portion in the first direction than any one of said first hollow protrusions.

* * * * *